US006783974B2

(12) United States Patent
Monahan et al.

(10) Patent No.: US 6,783,974 B2
(45) Date of Patent: Aug. 31, 2004

(54) MICROPLATE HAVING A LUBRICIOUS SURFACE AND METHODS FOR MAKING AND USING SUCH MICROPLATES

(75) Inventors: Beth C. Monahan, Painted Post, NY (US); Everett W. Coonan, Painted Post, NY (US)

(73) Assignee: Corning Incorporated, Corning, NY (US)

( * ) Notice: Subject to any disclaimer, the term of this patent is extended or adjusted under 35 U.S.C. 154(b) by 389 days.

(21) Appl. No.: 09/901,351

(22) Filed: Jul. 9, 2001

(65) Prior Publication Data

US 2002/0022263 A1 Feb. 21, 2002

Related U.S. Application Data

(60) Provisional application No. 60/217,442, filed on Jul. 10, 2000.

(51) Int. Cl.[7] .................................................. C12M 1/00

(52) U.S. Cl. ................ 435/288.4; 435/91.4; 435/305.2; 422/102; 264/328.17

(58) Field of Search ........................... 435/288.4, 305.2, 435/305.3, 6, 287.2, 91.4; 422/102; 264/328.17

(56) References Cited

U.S. PATENT DOCUMENTS 5,006,368 A * 4/1991 Louks ........................ 427/189
5,149,484 A * 9/1992 Ealer ..................... 264/328.17
6,093,559 A 7/2000 Bookbinder et al. ........ 435/183
6,130,279 A * 10/2000 Suzuki et al. ............... 524/401
6,340,589 B1 * 1/2002 Turner et al. ............ 435/287.2
6,555,792 B1 * 4/2003 Elsener et al. .............. 219/428

* cited by examiner

*Primary Examiner*—William H. Beisner
(74) *Attorney, Agent, or Firm*—William J. Tucker

(57) ABSTRACT

A microplate is described that has a surface with an enhanced lubricious property which makes it easier to remove the microplate from a thermocycler. Basically, the microplate has a frame which includes an array of wells formed therein that are made from a thermoplastic material (e.g. polypropylene) mixed with a non-toxic surface active material (e.g., surfactant, stearyl alcohol). The non-toxic surface active material functions to enhance the lubricity of the surface of the microplate which makes it easier to remove the microplate from the thermocycler. In addition, the non-toxic surface active material within the microplate also makes it easier to remove a newly molded microplate from a mold cavity in an injection molding machine. Also described herein are details about methods for making and using such microplates.

30 Claims, 4 Drawing Sheets

MICROPLATE HAVING A LUBRICIOUS SURFACE AND METHODS FOR MAKING AND USING SUCH MICROPLATES

CLAIMING BENEFIT OF PRIOR FILED PROVISIONAL APPLICATION

This application claims the benefit of U.S. Provisional Application Serial No. 60/217,442, filed on Jul. 10, 2000.

BACKGROUND OF THE INVENTION

1. Field of the Invention

The present invention relates in general to the biotechnology field and, in particular, to a microplate having a surface with an enhanced lubricious property and methods for making and using such microplates.

2. Description of Related Art

Today polymerase chain reaction (PCR) processes which are associated with replicating genetic material such as DNA and RNA are carried out on a large scale in both industry and academia, so it is desirable to have an apparatus that allows the PCR process to be performed in an efficient and convenient fashion. Because they are relatively easy to handle and low in cost, microplates are often used during the PCR process. A traditional microplate is typically made of a polymeric material and has an array of conical or bullet shaped wells.

In accordance with the PCR process, a small quantity of genetic material and a solution of reactants are deposited within each well of the traditional microplate. The traditional microplate is then placed in a thermocycler which operates to cycle the temperature of the contents within the wells. In particular, the traditional microplate is placed on a metal heating fixture in the thermocycler that is shaped to closely conform to the underside of the traditional microplate and, in particular, to the exterior portion of the wells. A heated top plate of the thermocycler then tightly clamps the traditional microplate onto the metal heating fixture while the contents in the traditional microplate are repeatedly heated and cooled for around 90–150 minutes. Because, of the close fit between the traditional microplate and the metal heating fixture and the tendency of the traditional microplate to change dimensions during the thermal cycling, it is often difficult for a scientist to remove the traditional microplate from the thermocycler. This sticking can adversely affect the integrity of the PCR process. Moreover, the sticking of the traditional microplate to the thermocycler can be especially troublesome if a robotic handling system is used to remove the traditional microplate from the thermocycler. Accordingly, there is and has been a need for a microplate that can be easily removed from a thermocycler. This need and other needs are satisfied by the microplate and the methods of the present invention.

BRIEF DESCRIPTION OF THE INVENTION

The present invention includes a microplate that has a surface with an enhanced lubricious property which makes it easier to remove the microplate from a thermocycler. Basically, the microplate has a frame which includes an array of wells formed therein that are made from a thermoplastic material (e.g. polypropylene) mixed with a non-toxic surface active material (e.g., surfactant, stearyl alcohol). The non-toxic surface active material functions to enhance the lubricity of the surface of the microplate which makes it easier to remove the microplate from the thermocycler. In addition, the non-toxic surface active material within the microplate also makes it easier to remove a newly molded microplate from a mold cavity in an injection molding machine. The present invention also includes methods for making and using such microplates.

BRIEF DESCRIPTION OF THE DRAWINGS

A more complete understanding of the present invention may be had by reference to the following detailed description when taken in conjunction with the accompanying drawings wherein.

DETAILED DESCRIPTION OF THE DRAWINGS

Referring to FIGS. 1-5, there are disclosed a preferred embodiment of a microplate and preferred methods for making and using the microplate. Although the microplate of the present invention is described as being used in a PCR process, it should be understood that the microplate can be used in any process that can benefit from the use of a microplate that has a lubricious surface.

Figure 1A:
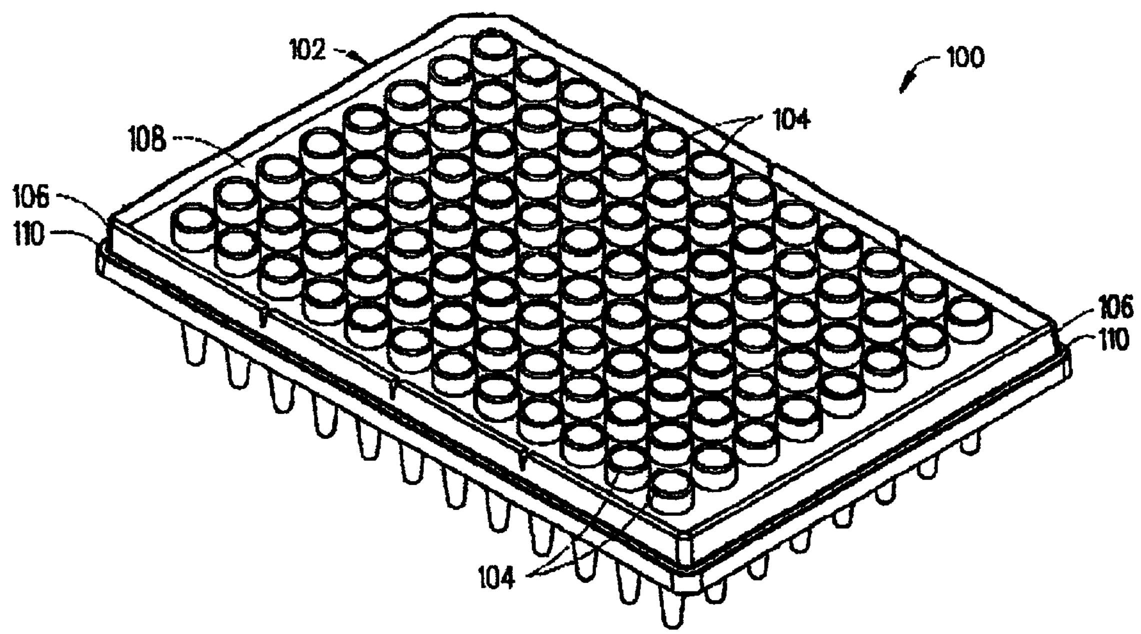
FIGS. 1A through 1C respectively illustrate a perspective view, a cut-away partial perspective view and a cross-sectional side view of a microplate in accordance with the present invention.
Figure 1B:
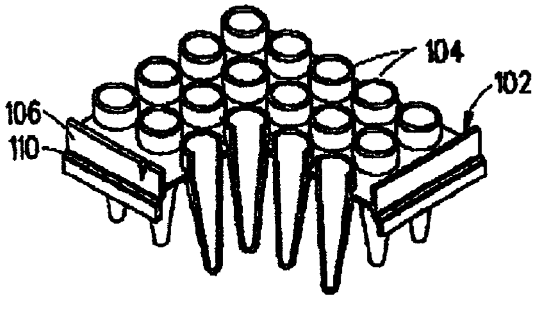
Figure 1C:
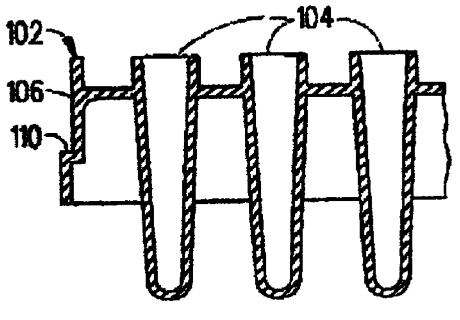

Referring to FIGS. 1A through 1C, there are illustrated different views of a microplate 100 in accordance with the present invention. Basically, the microplate 100 is manufactured from a thermoplastic material (e.g. polypropylene) that has been mixed with a small amount of non-toxic surface active material (e.g., surfactant, stearyl alcohol). The non-toxic surface active material functions to enhance the lubricity of the surface of the microplate 100 which makes it easier to handle the microplate 100. A more detailed discussion about the materials that can be used to make the microplate 100 is provided below after a brief discussion about an exemplary structure of the microplate 100 and the PCR process.

As shown, the microplate 100 includes a frame 102 that supports an array of ninety-six wells 104 each of which has a conical or bullet shape. The frame 102 which is rectangular in shape includes an outer wall 106 and a top planar surface 108 extending between the outer wall 106 and the wells 104. However, it should be understood that the frame 102 can be provided in any number of other geometrical shapes (e.g., triangular or square) depending on the desired arrangement of the wells 104. The outer wall 106 also has a rim 110 to accommodate the skirt of a microplate cover (not shown). The microplate 100 is configured to be placed within a thermocycler 200 which is described in greater detail below with respect to FIG. 2.

Figure 2:
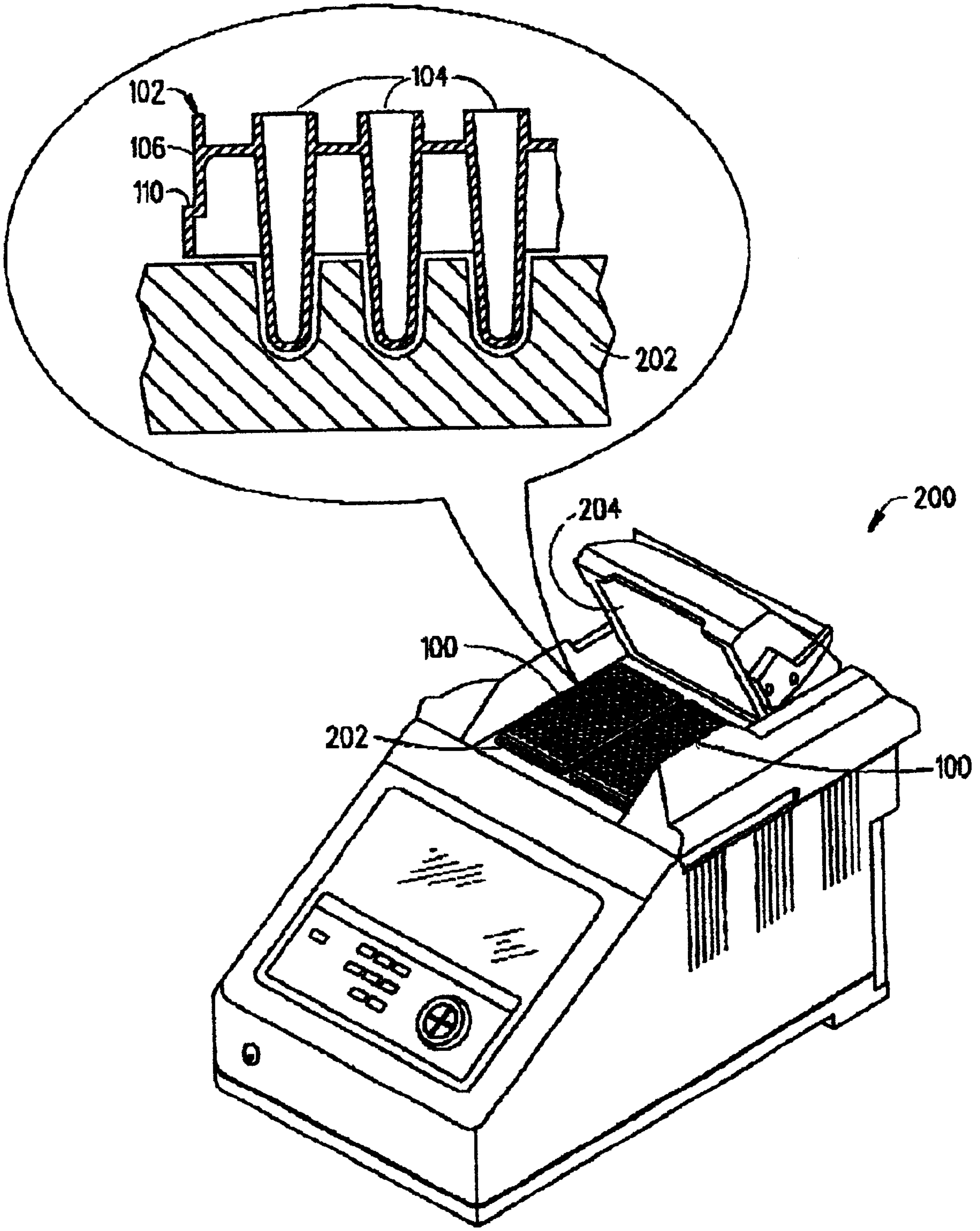
FIG. 2 is a perspective view of an exemplary thermocycler capable of heating and cooling the microplate shown in FIG. 1.

Referring to FIG. 2, there is a perspective view of a thermocycler 200 capable of heating and cooling one or more microplates 100 (only two shown). In accordance with the PCR process, a small quantity of genetic material and a solution of reactants are deposited within each well 104 of the microplate 100. The microplate 100 is then covered by a microplate cover (not shown) or some other type of seal to help prevent the evaporation of the contents within the wells 104. Thereafter, the microplate 100 is placed in the thermocycler 200 (e.g., GeneAmp® PCR System 9700) which operates to cycle the temperature of the contents within the wells 104. In particular, the microplate 100 is positioned onto a metal heating fixture 202 of the thermocycler 200 which has a series of cavities that are shaped to closely conform to the exterior portion of the wells 104 in the microplate 100 (see enlarged cross-sectional side view of the metal heating fixture 202 and microplate 100). The thermocycler 200 also has a heated top plate 204 (shown in the open position) that tightly clamps the microplate 100 onto the metal heating fixture 202 before the thermocycler 200 repeatedly heats and cools the contents within the microplate 100. For instance, the thermocycler 200 can cycle the temperature of the contents within the wells 104 from 95° C. to 55° C. to 72° C. some thirty times during the PCR process.

The use of a microplate 100 that has a surface with an enhanced lubricious property makes it easy for a scientist or robot handling system to remove the microplate 100 from the thermocycler 200 after completion of the PCR process. This is a marked improvement over the traditional microplate that had a tendency to stick to the metal heating fixture 202 of the thermocycler 200 which made it difficult for the scientist or robot handling system to remove the traditional microplate from the thermocycler 200.

The microplate 100 can be manufactured to have a lubricious surface by making it from a thermoplastic material such as polypropylene that has been mixed with a non-toxic surface active material such as a surfactant or stearyl alcohol. In the preferred embodiment, the microplate 100 is made from a melt blend of 0.25 wt. % to 0.5 wt. % of a surfactant (e.g., NOVEL II 18-1 manufactured by Condea Vista Company) that has been mixed with polypropylene (e.g., ACHIEVE™ 1615 manufactured by ExxonMobil). However, it should be understood that the optimum concentration of the non-toxic surface active material relative to the amount of thermoplastic material depends on the types of non-toxic surface active material and thermoplastic material. Table 1 illustrates some of the properties of the polypropylene sold under the brand name of ACHIEVE™ 1615:

TABLE 1

| | ASTM Method | Typical Values (1) | SI Units |
|---|---|---|---|
| Resin Properties | | | |
| Melt Flow Rate (230° C./2.16 kg) | D 1238 | 34 g/10 min | |
| Density | D 792 | 0.90 $g/cm^3$ | |
| DSC Melting Temperature | Exxon Mobil Method | 151° C. | |
| Molecular Weight Distribution | | Narrow | |
| Mechanical Properties (2) | | | |
| Tensile Strength @ Yield (2 in/min, 50 mm/min) | D 638 | 5.2 kpsi | 36 MPa |
| Elongation @ Yield (2 in/min, 50 mm/min) | Exxon Mobil Method | 13% | |

TABLE 1-continued

| | ASTM Method | Typical Values (1) | SI Units |
|---|---|---|---|
| Flexural Modulus, 1% Secant (0.05 in/min, 1.3 mm/min) | D 790A | 223 kpsi | 1538 MPa |
| Izod Impact Strength Notched, @ 23° C. (73° F.) | D 256 Method A | 0.5 ft-lb/in | 27 J/m |
| Thermal Properties | | | |
| Heat Deflection Temperature @ 66 psi, 455 kPa | D 648 | 237° F. | 114° C. |

1. Values given are typical and should not be interpreted as specification.
2. Mechanical properties were measured on injection molded ASTM parts.

Table 2 illustrates some of the properties of the surfactant sold under the brand name NOVEL II 18-1:

TABLE 2

| Novel II 18-1 (Surfactant) | Minimum | Maximum |
|---|---|---|
| Water, Wt % | | 0.1 |
| Hydroxyl Number, mg KOH/gram | 177 | 188 |
| pH, 5% in 1 PA/Water | 6 | 8 |
| Color, APHA | | 50 |

It should be understood that the preferred surfactant sold under the brand name NOVEL II 18-1 is in the category of surfactants called polyoxyethylene (POE) fatty ethers. More specifically, the NOVEL II 18-1 is one of the many POE stearyl ethers having the general structure $CH_3(CH_2)_{17}$—$(OCH_2CH_2)_n$—OH. As n increases, the hydrophilic-lipophilic balance number (HLB) and water solubility increase. As such, a surfactant having a HLB number which is less than 2 is preferred so as to minimize the potential for extraction of the surfactant into the contents of the wells 104 during the PCR process.

A series of tests have been performed on different types of microplates 100 after which it was determined that there are no detectable extracted surfactants found in the contents of the microplates 100. In the tests, a traditional microplate and several microplates 100 had wells filled with 40 $\mu$l of 0.01 M Tris buffer pH 8.3. The microplates where placed in a GeneAmp® PCR System 9700 thermocycler which cycled the temperature of the contents within the microplates from 95° C. to 55° C. to 72° C. some thirty times. After cycling the temperature, the buffer was removed from the traditional microplate and microplates 100 and submitted to an HPLC analysis. The HPLC analysis quantified how much, if any, of the NOVEL II 18-1 surfactant was present within the removed buffer for nine different microplates (see TABLE 3). The sample buffers were analyzed using normal phase chromatography with a methylene chloride and isopropanol gradient system. The samples were quantified using a calibration curve with a range of 0.016–2.0 mg/ml. A known test concentration solution of 2.03 mg/ml was analyzed to verify the calibration curve. The results of the test concentration solution were calculated to be 1.98, 2.04 and 2.03 mg/ml. All the sample buffers from microplates 100 were clean in that they did not contain any detectable levels of the NOVEL II 18-1 surfactants. The results were confirmed by mass spectrometry. Table 3 illustrates a summary of the aforementioned HPLC test results:

TABLE 3

| Sample | Concentration of extracted surfactants (NOVEL II 18-1) μg/ml |
|---|---|
| AB gene control plate 384 well | BDL |
| HDPE control plate 384 well | BDL |
| Microplate 100 (ACHIEVE ™ 1615 + 0.5% NOVEL II 18-1)-plate #1 | BDL |
| Microplate 100 (ACHIEVE ™ 1615 + 0.5% NOVEL II 18-1)-plate #2 | BDL |
| Microplate 100 (ACHIEVE ™ 1615 + 0.5% NOVEL II 18-1)-plate #3 | BDL |
| Microplate 100 (ACHIEVE ™ 1615 + 0.5% NOVEL II 18-1 15 days @ 20° C.)-sample #1 | BDL |
| Microplate 100 (ACHIEVE ™ 1615 + 0.5% NOVEL II 18-1 15 days @ 20° C.)-sample #2 | BDL |
| Microplate 100 (ACHIEVE ™ 1615 + 0.5% NOVEL II 18-1 15 days @ 65° C.)-sample #1 | BDL |
| Microplate 100 (ACHIEVE ™ 1615 + 0.5% NOVEL II 18-1 15 days @ 65° C.)-sample #2 | BDL |

BDL (Below Detection Limits) = 16 μg/ml

A variety of non-toxic surface active materials now known or subsequently developed can be combined with a thermoplastic material used to make the microplate 100. Examples of suitable non-toxic surface active materials can include other surfactants, ethoxylated fatty alcohols, esters of fatty acids. solid silicones (UHMW), fluoropolymers, fatty alcohols, stearyl alcohol, various other waxes and other materials known to be effective internal lubricant agents.

Examples of the types of thermoplastic materials which can be used to manufacture the microplate 100 can include those comprising or composed of polystyrene, polypropylene, polymethyl methacrylate, polyvinyl chloride, polymethyl pentene, polyethylene, polycarbonate, polysulfone, polystyrene copolymers (e.g., SAN and ABS), polypropylene copolymers, fluoropolymers, polyamides, silicones, and elastomers, including silicone, hydrocarbon, and fluorocarbon elastomers.

Figure 3:
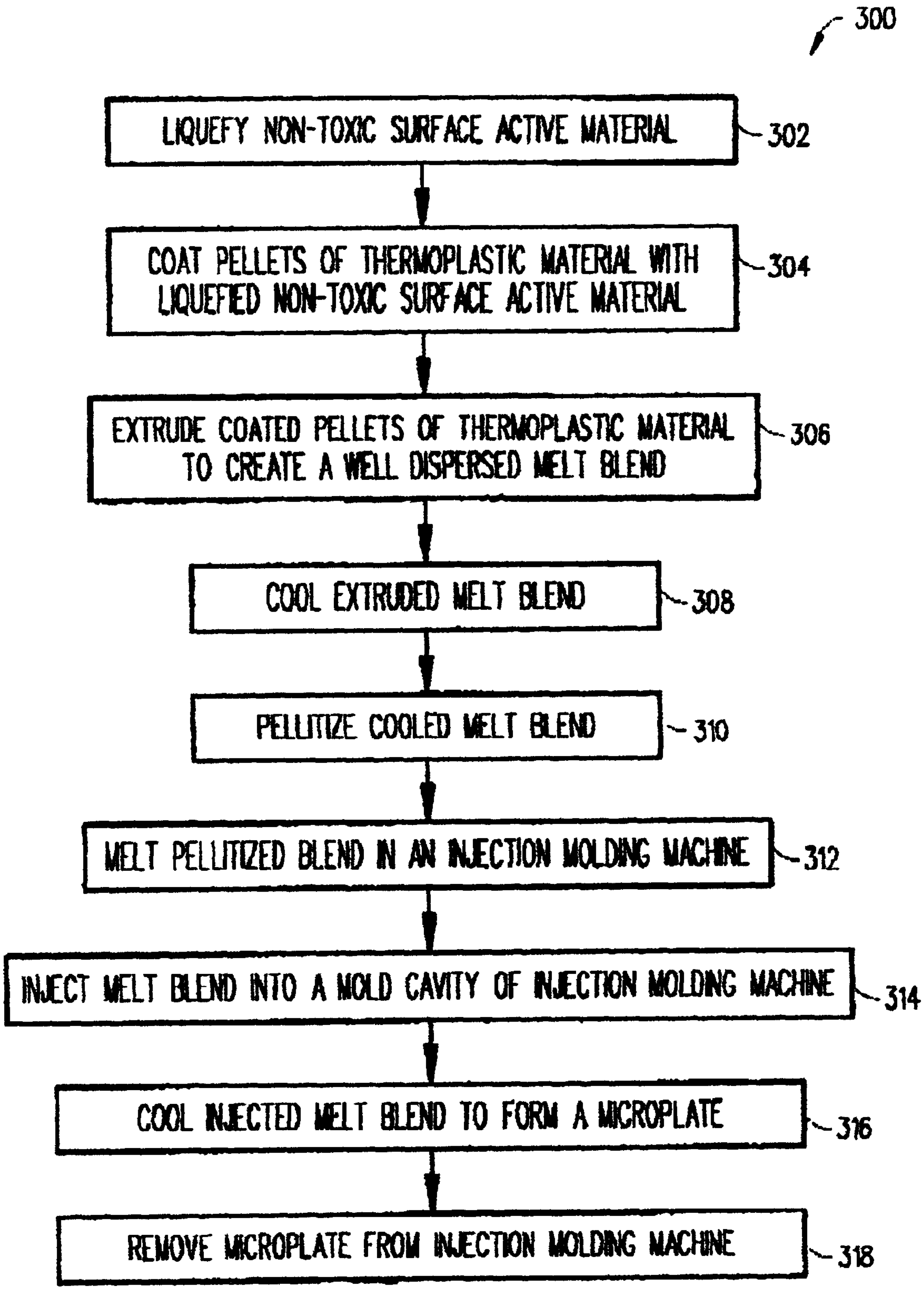
FIG. 3 is a flowchart illustrating the steps of a preferred method for making the microplate shown in FIG. 1 in accordance with the present invention.

Referring to FIG. 3, there is a flowchart illustrating the steps of the preferred method 300 for making the microplate 100. Although the microplate 100 that has been described herein has ninety-six functional wells arranged in a grid having a plurality of rows and columns, it should be understood that the present invention is not limited to these arrangements. Instead, the present invention can be implemented in any type of microplate arrangement and is not limited to any specific number of wells.

The microplate 100 can be manufactured by liquefying (step 302) a non-toxic surface active material and coating (step 304) pellets of a thermoplastic material with the liquefied non-toxic surface active material. Again, the preferred microplate 100 is manufactured from a thermoplastic material such as polypropylene and a non-toxic surface active material such as stearyl alcohol or surfactants having an HBL which is less then 2. In particular, the preferred microplate 100 is manufactured from polypropylene and between 0.25 wt. % and 0.5 wt. % of NOVEL II 18-1 surfactants the amount of which can be chosen so as to minimize the potential of extraction of the surfactant during the PCR process.

The next step in manufacturing the microplate 100 includes extruding (step 306) the pellets of thermoplastic material that are coated with the non-toxic surface active material to create a melt blend. In particular, the coated pellets of thermoplastic material can be fed into a twin-screw extruder with the help of a gravimetric feeder to create a well dispersed melt blend. The extruded melt blend is then run through a water bath and cooled (step 308) before being pelletized (step 310) and dried at approximately 50° C. for a period of time such as ten hours. The pelletized melt blend is heated and melted (step 312) by an injection molding machine which then injects (step 314) the melt blend into a mold cavity of the injection molding machine. The mold cavity includes sections shaped to form the microplate 100. The injection molding machine then cools (step 316) the injected melt blend to create the microplate 100. Finally, the microplate 100 is removed (step 318) from the injection molding machine.

Another advantage of the microplate 100 having a lubricious surface is that the microplate 100 can be easily removed from the mold cavity of the injection molding machine. This is a marked improvement over the state of the art where the traditional microplate would warp and distort upon removal from the mold cavity because it would stick to the mold cavity. In addition, the injection molding machine can be more productive in making microplates 100 since it has shorter molding cycles because the newly molded microplates 100 can be easily removed from the mold cavity (see FIG. 4). Moreover, the larger the number of wells 104 in the microplate 100 the more lubricious surface area there is and as such the easier it is to remove the microplate 100 from the mold cavity when compared to same sized traditional microplates.

Figure 4:
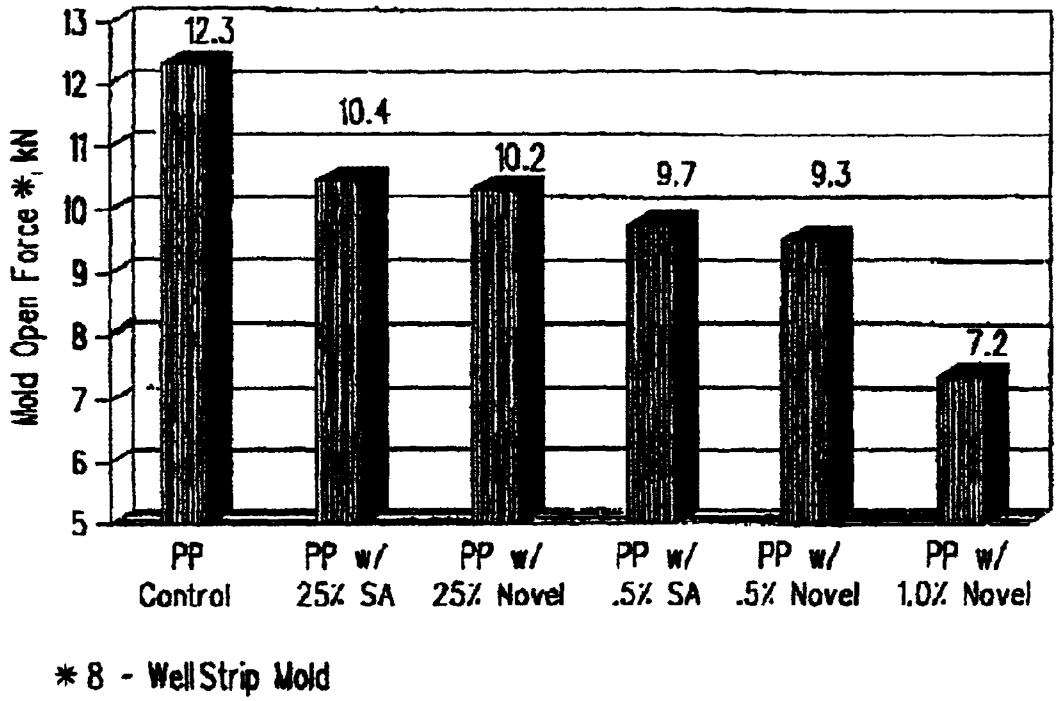
FIG. 4 is a graph illustrating the different forces it takes to remove different types of microplates from an injection molding machine.

Referring to FIG. 4, there is a graph illustrating the different forces it takes to remove different types of microplates 100 from an injection molding machine. As shown, a traditional microplate (PP Control) had a 12.3 kN mold open force which is greater than the mold open forces associated with different types of microplates 100. In particular, in terms of mold release, the microplates 100 including stearyl alcohol (SA) are nearly as effective as the microplates 100 including the additive NOVEL II 18-1 surfactant. Since stearyl alcohol does not extract during PCR, it is clearly a desirable alternative to the Novel II 18-1 surfactant additive.

Normally, one would characterize mold release properties by measuring the force required to eject the parts from the mold (ejection force). In this experiment, however, the cores (mold pins which form the inside of the wells) are on the stationary side of the injection molding machine. Therefore, the force required to open the mold (mold open force) was chosen as the indicator of relative frictional force between the mold surface and the microplate. Using standard molding conditions, the traditional microplate made from Achieve™ 1615 polypropylene was molded first. The hydraulic pressure for mold opening was reduced until the force was insufficient to open the mold at the end of cooling time. The force, below which the mold would not open, was recorded as the minimum mold open force. This point was then determined for each of the microplates 100 made from Achieve™ 1615 blends containing different amounts of either stearyl alcohol or Novel II 18-1 surfactants. The mold surfaces were washed thoroughly with isopropanol between each test.

Figure 5:
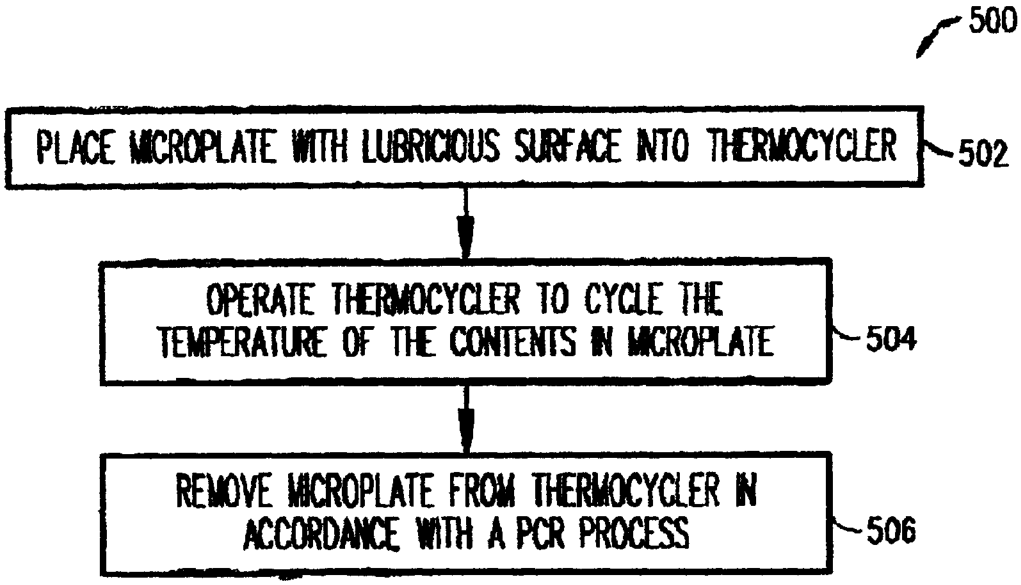
FIG. 5 is a flowchart illustrating the steps of a preferred method for using the microplate shown in FIG. 1 in accordance with the present invention.

Referring to FIG. 5, there is a flowchart illustrating the steps of a preferred method 500 for using the microplate 100. Although the microplate 100 of the present invention is described as being used in a PCR process, it should be understood that the microplate 100 can be used in any process that can use a microplate that has a lubricious surface.

Beginning at step 502, the scientist or robotic handling system places the microplate 100 into the thermocycler 200.

The robotic handling system can handle the microplate 100 if the microplate 100 has a correctly sized footprint. Prior to placing the microplate 100 into a thermocycler 200, the scientist can deposit a small quantity of genetic material and a solution of reactants into each well 104 of the microplate 100. And, then the scientist can place a microplate cover or some other type of seal over the microplate 100 to help prevent the evaporation of the contents within the wells 104.

At step 504, the thermocycler 200 operates and cycles the temperature of contents within the wells 104 of the microplate 100 in accordance with the PCR process. For instance, the thermocycler 200 can cycle the temperature of the contents within the wells 104 from 95° C. to 55° C. to 72° C. some thirty times during the PCR process.

Lastly at step 508, the scientist or robotic handling system then removes the microplate 100 from the thermocycler 200, wherein the non-toxic surface active material within the microplate 100 enhances a lubricious property of a surface of microplate 100 which makes it easier to remove the microplate 100 from the thermocycler 200. Again, this is a marked improvement over the traditional microplate that had a tendency to stick to the thermocycler 200 which made it difficult for the scientist or robot handling system to remove the traditional microplate from the thermocycler 200.

It should be understood that the benefits of surface lubricity of the present invention could be achieved by coating the underside of a traditional PCR microplate using the same non-toxic surface active materials described above. Moreover, this approach has the advantage of allowing a wider choice of non-toxic surface active materials, since these materials do not contact the contents in the wells of the microplate is involved.

Although one embodiment of the present invention has been illustrated in the accompanying Drawings and described in the foregoing Detailed Description, it should be understood that the invention is not limited to the embodiment disclosed, but is capable of numerous rearrangements, modifications and substitutions without departing from the spirit of the invention as set forth and defined by the following claims.

What is claimed is:

1. A microplate, comprising:

a frame including a plurality of wells formed therein, said frame is manufactured from a thermoplastic material that has been mixed with a non-toxic surface active material that can enhance a lubricious property of a surface of said frame which makes it easier to remove said frame from a thermocycler, wherein said non-toxic surface active material has a percentage of weight relative to the thermoplastic material that was determined in order to minimize extraction of said non-toxic surface active material into the wells of said frame during the operation of the thermocycler.

2. The microplate of claim 1, wherein said frame can be easily removed from an injection molding machine.

3. The microplate of claim 1, wherein said non-toxic surface active material is a surfactant.

4. The microplate of claim 3, wherein said surfactant has a hydrophilic-lipophilic balance number which is less than two.

5. The microplate of claim 1, wherein said non-toxic surface active material is an ethoxylated fatty alcohol.

6. The microplate of claim 1, wherein said non-toxic surface active material is stearyl alcohol.

7. The microplate of claim 1, wherein said thermoplastic material is polypropylene.

8. The microplate of claim 1, wherein said non-toxic surface active material is an ester of a fatty acid.

9. The microplate of claim 1, wherein said non-toxic surface active material is a solid silicone.

10. The microplate of claim 1, wherein said non-toxic surface active material is a fluoropolymer.

11. The microplate of claim 1, wherein said non-toxic surface active material is an internal lubricant agent.

12. A microplate, comprising:

a frame including a plurality of wells formed therein, said frame is manufactured from a thermoplastic material that has been mixed with a non-toxic surface active material that can enhance a lubricious property of a surface of said frame which makes it easier to handle said frame, wherein said non-toxic surface active material is a surfactant and wherein said surfactant is a polyoxyethylene fatty ether.

13. The microplate of claim 12, wherein said polyoxyethylene fatty ether has a molecular structure of $CH_3(CH_2)_{17}$—$(OCH_2CH_2)_n$—OH.

14. A multiwell plate manufactured in such a way so as to improve the ability to properly carry out a polymerase chain reaction process, said multiwell plate comprising:

a frame including a plurality of wells formed therein, said frame is manufactured from a thermoplastic material that has been mixed with a non-toxic surface active that can enhance a lubricious property of a surface of said frame which makes it easier to remove said frame from a thermocycler, wherein said non-toxic surface active material has a percentage of weight relative to the thermoplastic material that was determined in order to minimize extraction of said non-toxic surface active material into the wells of said frame during the operation of the thermocycler.

15. The microplate of claim 14, wherein said non-toxic surface active material is a surfactant with a hydrophilic-lipophilic balance number of less than two.

16. The microplate of claim 14, wherein said non-toxic surface active material is stearyl alcohol.

17. The microplate of claim 14, wherein said thermoplastic material is polypropylene.

18. The microplate of claim 14, wherein said frame has a footprint capable of being handled by a robotic handling system.

19. A multiwell plate manufactured in such a way so as to improve the ability to properly carry out a polymerase chain reaction process, said multiwell plate comprising:

a frame including a plurality of wells formed therein, said frame is manufactured from a thermoplastic material that has been mixed with a non-toxic surface active that can enhance a lubricious property of a surface of said frame which makes it easier to remove said frame from a thermocycler, wherein said non-toxic surface active material is a surfactant and wherein said surfactant is a polyoxyethylene fatty ether that has a molecular structure of $CH_3(CH_2)_{17}$—$(OCH_2CH_2)_n$—OH.

20. A method for making a microplate, said method comprising the steps of:

liquefying a non-toxic surface active material;

coating pellets of thermoplastic material with said liquefied non-toxic surface active material;

extruding said pellets of thermoplastic material coated with said non-toxic surface active material to create a melt blend;

cooling said extruded melt blend;

pelletizing said cooled melt blend;

melting said pelletized melt blend;

injecting said melted blend into a mold cavity of an injection molding machine, said mold cavity includes sections shaped to form said microplate;

cooling the injected melt blend to create said microplate; and removing said microplate from the injection molding machine, wherein the non-toxic surface active material enhances a lubricious property of a surface of said microplate which makes it easier to remove said microplate from the injection molding machine and wherein said non-toxic surface active material has a percentage of weight relative to the thermoplastic material that was determined in order to minimize extraction of said non-toxic surface active material into wells of said microplate while said microplate is located within an operating thermocycler.

21. The method of claim 20, wherein said non-toxic surface active material is a surfactant with a hydrophilic-lipophilic balance number of less than two.

22. The method of claim 20, wherein said non-toxic surface active material is stearyl alcohol.

23. The method of claim 20, wherein said thermoplastic material is polypropylene.

24. A method for making a microplate, said method comprising the steps of:

liquefying a non-toxic surface active material;

coating pellets of thermoplastic material with said liquefied non-toxic surface active material;

extruding said pellets of thermoplastic material coated with said non-toxic surface active material to create a melt blend;

cooling said extruded melt blend;

pelletizing said cooled melt blend;

melting said pelletized melt blend;

injecting said melted blend into a mold cavity of an injection molding machine, said mold cavity includes sections shaped to form said microplate;

cooling the injected melt blend to create said microplate; and removing said microplate from the injection molding machine, wherein the non-toxic surface active material enhances a lubricious property of a surface of said microplate which makes it easier to remove said microplate from the injection molding machine, wherein said non-toxic surface active material is a surfactant which is a polyoxyethylene fatty ether that has a molecular structure of $CH_3(CH_2)_{17}$—$(OCH_2CH_2)_n$—OH.

25. A method for using a microplate, said method comprising the steps of:

placing the microplate into a thermocycler, said microplate includes:

a frame having a plurality of wells formed therein, said microplate is manufactured from a combination of thermoplastic material and non-toxic surface active material;

operating the thermocycler so as to cycle the temperature of contents within the wells of said microplate; and removing the microplate from the thermocycler, wherein the non-toxic surface active material enhances a lubricious property of a surface of said microplate which makes it easier to remove said microplate from the thermocycler and wherein said non-toxic surface active material has a percentage of weight relative to the thermoplastic material that was determined in order to minimize extraction of said non-toxic surface active material into the wells of said frame during the operation of the thermocycler.

26. The method of claim 25, wherein said microplate is manufactured in such a way so as to improve the ability to properly carry out a polymerase chain reaction process.

27. The method of claim 25, wherein said non-toxic surface active material is a surfactant with a hydrophilic-lipophilic balance number of less than two.

28. The method of claim 25, wherein said non-toxic surface active material is stearyl alcohol.

29. The method of claim 25, wherein said thermoplastic material is polypropylene.

30. A method for using a microplate, said method comprising the steps of:

placing the microplate into a thermocycler, said microplate includes:

a frame having a plurality of wells formed therein, said microplate is manufactured from a combination of thermoplastic material and non-toxic surface active material;

operating the thermocycler so as to cycle the temperature of contents within the wells of said microplate; and removing the microplate from the thermocycler, wherein the non-toxic surface active material enhances a lubricious property of a surface of said microplate which makes it easier to remove said microplate from the thermocycler, wherein said non-toxic surface active material is a surfactant which is a polyoxyethylene fatty ether that has a molecular structure of $CH_3(CH_2)_{17}$—$(OCH_2CH_2)_n$—OH.

* * * * *